United States Patent [19]

de Bruyne

[11] 4,204,774

[45] May 27, 1980

[54] SYNCHRONOUS STIRRER

[76] Inventor: Norman A. de Bruyne, 3700 Brunswick Pike, Princeton, N.J. 08540

[21] Appl. No.: 15,366

[22] Filed: Feb. 26, 1979

[51] Int. Cl.² .................... B01F 15/06; B01F 13/02; B01F 13/08
[52] U.S. Cl. .................................. 366/102; 366/147; 366/242; 366/273
[58] Field of Search ............... 366/147, 243, 244, 261, 366/273, 276, 277, 278, 287, 101, 102, 242

[56] References Cited

U.S. PATENT DOCUMENTS

| | | | |
|---|---|---|---|
| 2,539,436 | 1/1951 | Kost | 366/287 |
| 3,332,669 | 7/1967 | Colonna | 366/258 |
| 3,484,204 | 12/1969 | Caviness | 366/139 |
| 3,913,895 | 10/1975 | Bruyne | 366/247 |
| 3,955,802 | 5/1976 | Bruyne | 366/243 |
| 3,998,435 | 12/1976 | Bruyne | 366/243 |
| 4,057,226 | 11/1977 | Koek | 366/287 |

*Primary Examiner*—Robert W. Jenkins

*Attorney, Agent, or Firm*—Richard C. Woodbridge

[57] ABSTRACT

A synchronous motor is employed to orbit one end of a stirring rod the other end of which is suspended by a flexible diaphragm in a liquid filled container. The synchronous motor includes a stator connected to a source of regular alternating current and a cylindrical permanent magnet rotor. A drive plate is connected across one end of the rotor. The stirring rod is received in an eccentrically located aperture in the plate so that one end of the rod is driven in a circle. The motor is connected to a mounting plate on the cap of the container by a pair of threaded studs. Springs surround each of the studs so that the distance between the motor and the cap can be altered by screwing up or down on a pair of wing nuts received on the studs. The diaphragm acts as a fulcrum for the stirring rod so that the linear velocity of the orbiting free end of the rod can be controlled by altering the distance between the motor and the cap. The device is relatively easy to clean and generates little heat compared with that of a magnetic stirrer.

15 Claims, 18 Drawing Figures

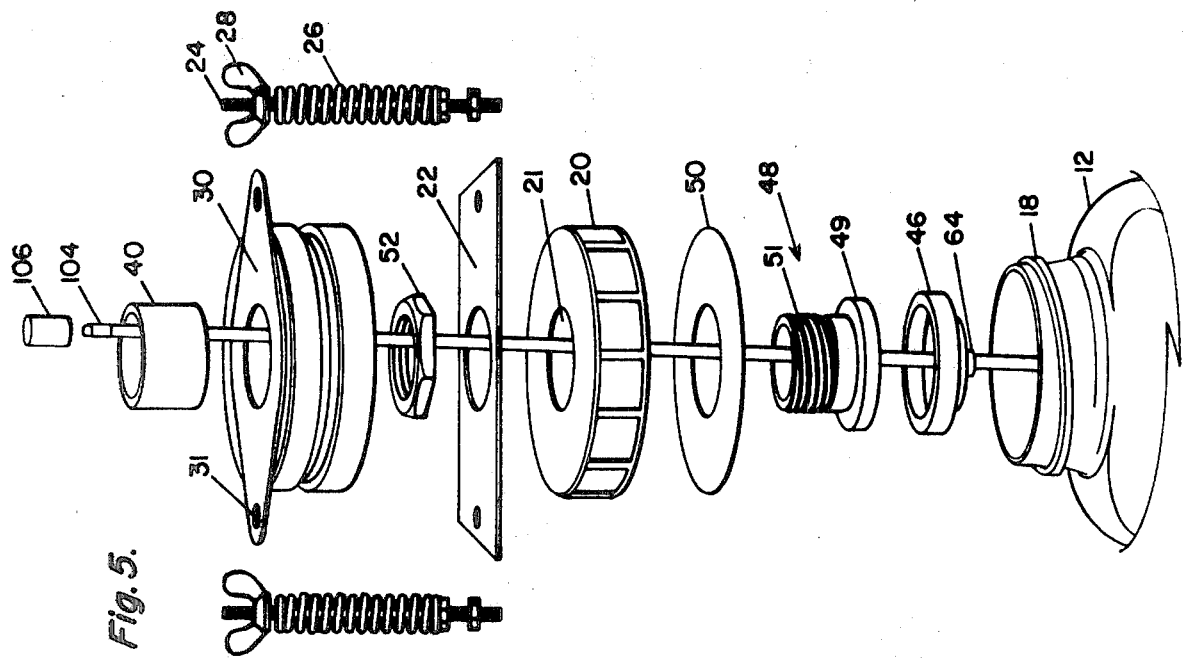
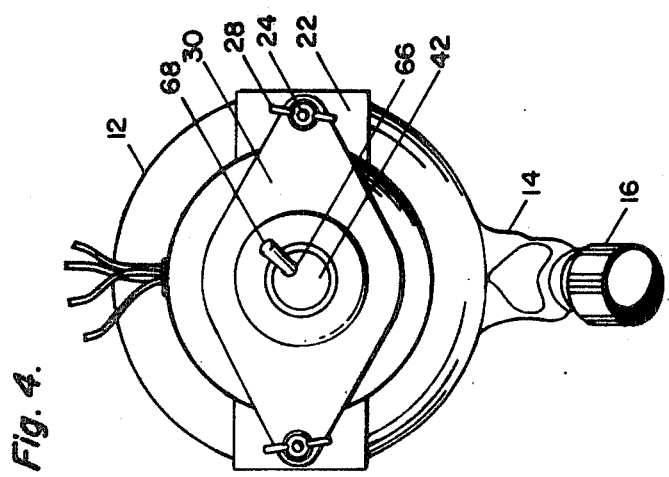

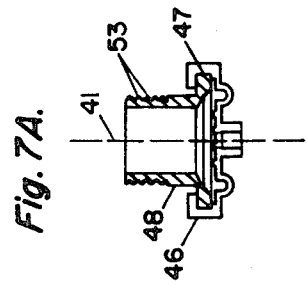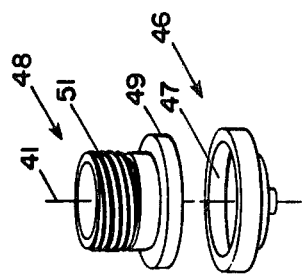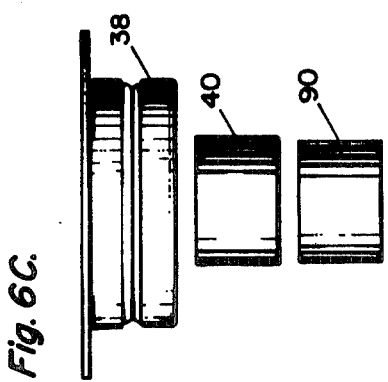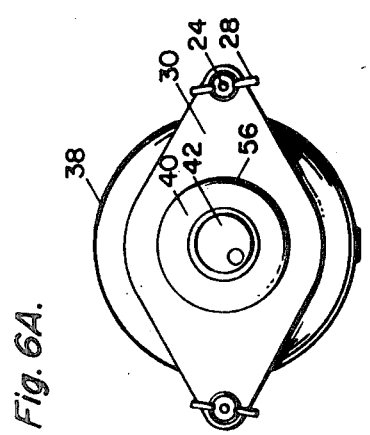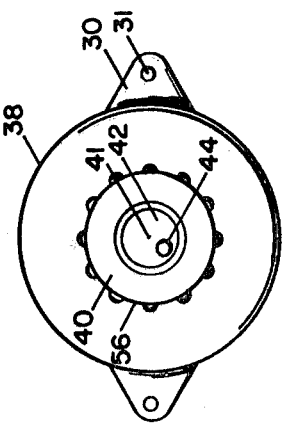

SYNCHRONOUS STIRRER

BACKGROUND OF THE INVENTION

1. Field of the Invention

This invention concerns a laboratory stirrer which includes a synchronous motor for driving a stirring rod.

2. Description of the Prior Art

A controlled temperature is an essential requirement for all tissue and cell culture in vitro and in cell suspension culture (widely used in cancer research). The media used as liquids for suspension cell culture range from horse serum to embryo extract to protein-free media. Most workers have gassed the culture with air containing 5% carbon dioxide. It is also necessary to be able to standardized the conditions of stirring. To do this there are several types of stirring apparatus which are well known to those of ordinary skill in the art.

One of the most common forms of stirring equipment is the magnetic stirrer. A typical magnetic stirrer comprises a plastic clad permanent bar magnet which is placed in the laboratory beaker and a base unit which produces a rotating magnetic field. The laboratory flask is placed upon the base unit and when the device is turned on, the permanent magnet is induced to whirl around inside the container. Unfortunately, such an approach has several drawbacks when used in the type of research outlined above. To avoid damaging the cells the rotating bar magnet has to be suspended clear of the base of the vessel and the bearings required eventually become clogged. Another drawback of conventional magnetic stirrers is that they generate a great deal of heat. It is generally desirable to maintain cell suspension cultures at a temperature between 35° C. and 36° C. Because magnetic stirrers create enough heat to unbalance certain sensitive cultures it is often necessary to provide heat shielding or refrigeration or both. Another disadvantage of such magnetic stirrers is that they cannot be immersed in a water bath.

In order to minimize the problems caused by heat and grinding this inventor had developed pneumatic equipment as described in U.S. Pat. No. 3,998,435 entitled "Oscillating Stirrers" and issued on Dec. 21, 1976. That device consists of three flexible diaphragms actuated by three phase alternating air (the analog of alternating electric current). These diaphragms are linked to a stirring rod and cause it to orbit and stir the culture medium. The following references were cited during the prosecution of U.S. Pat. Nos. 3,993,435: 3,332,669 issued July 1967 to Calonna; 3,484,204 issued December 1969 to Caviness; 3,913,895 issued October 1975 to Norman Adrian de Bruyne and 3,955,802 issued May 1976 to Norman Adrian de Bruyne.

Such pneumatic stirrers have several advantages. For example it is possible to put a pneumatic stirrer in a water bath. Conventional pneumatic stirrers using air motors cause problems because they discharge air to the atmosphere and hence cannot be used in incubators with a controlled carbon dioxide content. In contrast the inventor's pneumatic stirrer is a closed reciprocating device which entails no input or output of air to the atmosphere.

There are devices known to those of ordinary skill in the art for transmitting orbital motion into a vacuum vessel. See for example, FIG. 121 of Max Pollermann's "Bauelemente der Physikalische Technik" which discloses a nutating device for that purpose.

SUMMARY OF THE INVENTION

Briefly described the invention comprises a simple electromagnetic apparatus for stirring a laboratory liquid with a rod without generating appreciable heat. The liquid is preferably contained in a standard flask or beaker of the sort well known to those of ordinary skill in the art. A conventional cap having a hole therethrough is adapted to threadably engage the neck of the container. A silicone rubber diaphragm stretches across the opening of the cap and engages the circumferential flange of a cylindrical tubular element that extends through the cap opening. A mounting plate extends across the top of the cap and the whole cap assembly is held together by a washer and a nut which threadably engages the threaded end of the cylindrical element. The stirring rod is frictionally engaged in a hole in the center of the diaphragm so that the free end of the rod is suspended in a dependent fashion into the liquid on the interior of the flask.

A synchronous stator and rotor combination is held in position above the container cap by a pair of threaded studs which extend from the cap mounting plate to a plate rigidly connected to the stator element. Each of the studs is surrounded by a spring. The studs pass through a hole in the stator mounting plate and are secured therein by a pair of wing nuts. Accordingly, the distance between the synchronous motor and the cap can be infinitely adjusted by screwing up or screwing down on the wing nuts. The synchronous motor includes a permanent magnet rotor mounted therein which is adapted for rotation about a major axis. The rotor is generously lubricated by silicone grease so that the rotor element virtually floats within the stator element supported by the magnetic forces therein. Alternatively a Teflon ® bearing may be used in place of grease. Attached to the rotor is a small drive plate having an aperture therein whose center is offset from the major axis of rotation of the rotor. Accordingly, when the rotor rotates it carries the upper end of the glass rod around in a circular orbit. The diaphragm acts as a fulcrum during rotation so that the liquid contacting free end of the rod has a linear velocity and motion dictated entirely by the motion of the rotor and its distance from the cap. By moving the motor assembly upward it is possible to decrease the linear velocity of the free end of the stirring rod. Conversely, by decreasing the distance between the synchronuos motor and the cap it is possible to increase the linear velocity of the orbiting tip of the rod.

The stirrer rod is essentially a conical pendulum with its own natural frequency and it is advantageous though not essential to tune the pendulum to have a natural frequency of 300 revolutions per minute in order to get maximum transfer of energy from the motor. This can be done by positioning a small mass (30 grams) on the top end of the rod. This process of impedance matching is less important with the electric motor drive than with my pneumatic activator as the greater power of the electric motor allows it to produce forced oscillations.

These and other features of the present invention will be more fully understood with reference to the following drawings and detailed description of the preferred embodiment.

BRIEF DESCRIPTION OF THE DRAWINGS

FIG. 4 is a top plan view of the invention seen in FIG. 2.

FIG. 5 is an exploded perspective view of the preferred embodiment of the invention.

FIG. 6A is a top plan view of the synchronous stator and rotor combination.

FIG. 6B is a bottom plan view of the synchronous stator and rotor combination.

FIG. 6C is an exploded side elevational view of the synchronous stator and rotor combination.

FIG. 7A is a cross sectional view of the diaphragm in position on the threaded cylindrical mounting element.

FIG. 7B is an exploded view of the elements shown in FIG. 7A.

DETAILED DESCRIPTION OF THE PREFERRED EMBODIMENT

During the course of this description like numbers will be used to indicate like elements according to the different figures which illustrate the invention.

Figure 1:
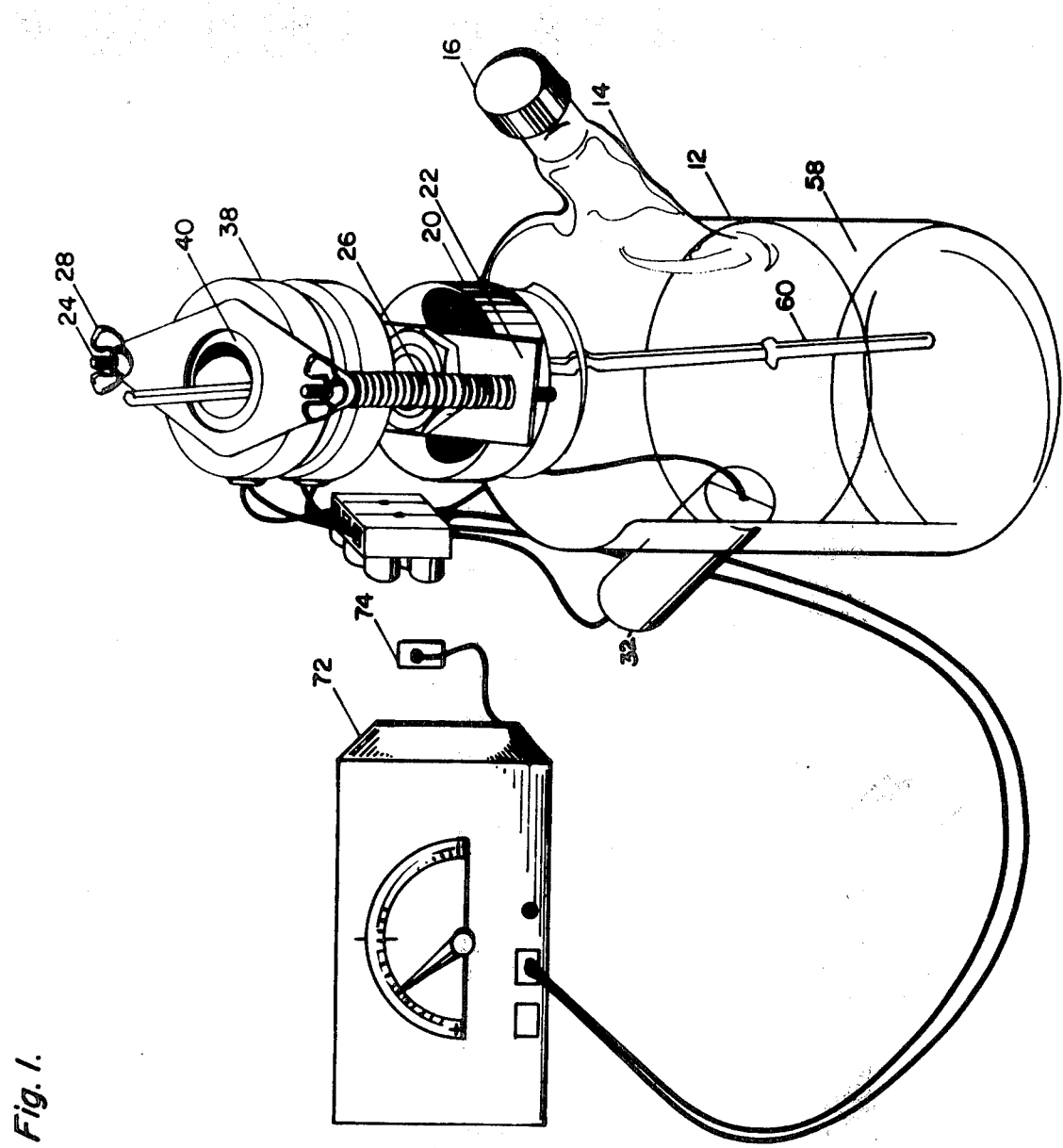
FIG. 1 is a general perspective view of the invention in position on top of a standard laboratory container.
Figure 2:
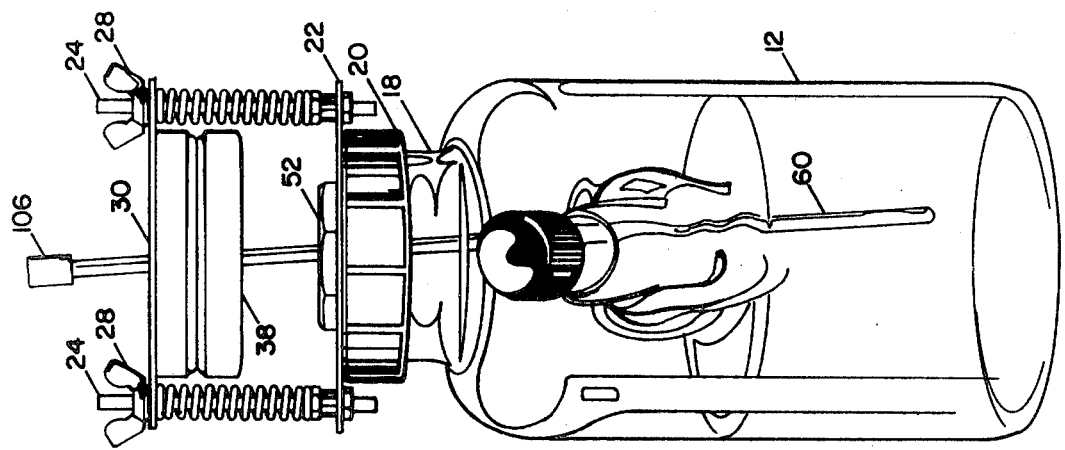
FIG. 2 is a left side elevational view of the invention in position on a container.
Figure 3:
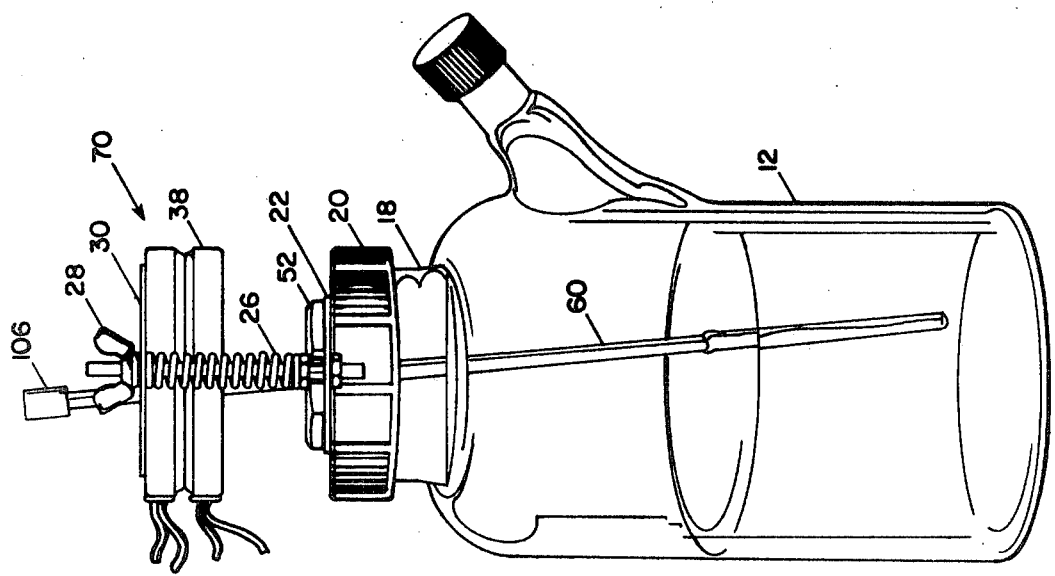
FIG. 3 is a front elevational view of the invention seen in FIG. 2.

FIG. 1 illustrates the manner in which the invention 10 is attached to a standard laboratory container 12. The container 12 may be a flask made for suspension cell culture of the sort known to those of ordinary skill in the art. A typical flask would include a sidearm 14, a sidearm cap 16, and a threaded neck 18. A suitable laboratory cell suspension culture or similar liquid 58 resides in the interior cavity of the container 12.

Cap 20 includes interior threads which are adapted to be received on the threaded neck 18 of the container 12. A cap mounting plate 22 is attached across the surface of cap 20 and serves as a platform for stand off studs 24 which support the synchronous motor assembly 70. Synchronous motor assembly 70 essentially comprises a stator 38 and rotor 40. Motor mounting plate 30 is firmly attached to stator 38 and includes a pair of holes 31 which receive the threaded ends of stand off studs 24. Each of the stand off studs 24 is surrounded by a spring 26 which extends from the top surface of cap mounting plate 22 to the under surface of motor mounting plate 30. A pair of wing nuts 28 are respectively received on the threaded ends of stand off 24. By screwing the wing nuts 28 upwardly or downwardly it is possible to adjust the distance of gap 76 between the synchronous motor assembly 70 and the flask cap 20. Stator 38 may be connected directly to a 110/120 volt AC 60 hertz power source such as a wall plug 74 by means of a conventional cord 34 and plug 36 combination. Capacitor 32 is connected across the winding of stator 38 in the manner well known to those of ordinary skill in the art to cause a 90° phase shift sufficient to produce the necessary synchronous rotating field within the stator. According to an alternative embodiment of the present invention it is possible to employ a variable frequency generator 72 as an alternate source of synchronous power. In this fashion it is possible to change the speed of the stirring rod 60 by altering the frequency of the power source.

Figure 10:
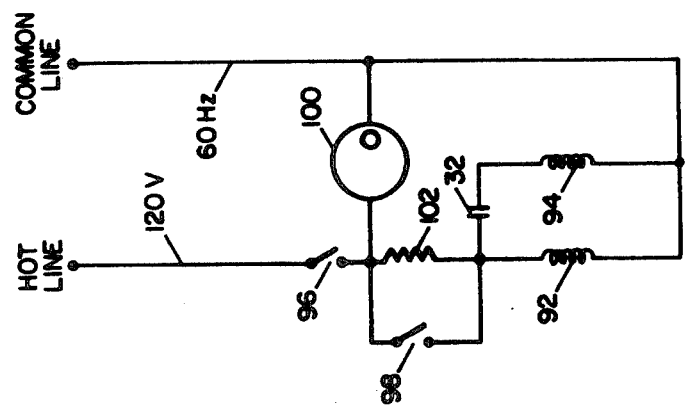
FIG. 10 is an electrical schematic of the present invention.

According to the preferred embodiment of the present invention the stator 38 and rotor 40 may be of the sort found in conventional synchronous clock motors. More particularly, a common 24 pole, synchronous clock motor produced by the North American Phillips Corporation was used in the preferred embodiment. The electrical connection of the motor assembly 70 to a power source is entirely conventional and is not deemed to be part of this invention. See FIG. 10. The stator 38 has 24 poles, i.e. 12 pole pairs, which at a supply frequency of 60 hertz produces a field which rotates at a speed of 300 r.p.m. or 5 rotations per second. The rotor 40 comprises a permanent magnet core in the form of a hollow cylinder. The major axis of rotation 41 of the rotor 40 coincides with the major axis of the cylinder. According to the preferred embodiment of the invention the rotor 40 is liberally packed with a silicone grease whose viscosity does not vary substantially with temperature. The stator 38 tends to magnetically support the rotor 40 in such a fashion that it floats within the stator cavity assisted by the silicone grease. It has also been found that one or two sheets of 0.0045 inch thick Teflon ® wrapped in a cylinder as shown in FIG. 6C acts as a satisfactory bearing 88.

A rotor drive plate or disc 42 is attached to the bottom end of rotor 40 and lies in a plane that is substantially perpendicular to the axis of rotation 41 of the rotor. An aperture 44 passes through drive plate 52 and is large enough to slidably receive a section 66 of the stirring rod 60. Aperture 44 is eccentrically located with respect to the axis of rotation 41 of the rotor 40. The rod should be a sloppy fit in hole 44. The driving and centrifugal forces keeps it engaged with one part of the circumference of the hole. Note that the rod 60 is always at an angle different from 90° with respect to the rotor drive plate 42. The important characteristic of the aperture is that the portion of the aperture 44 which engages the driven section 66 of the stirring rod 60 must be eccentrically located with respect to the axis of rotation 41. In addition the aperture 44 must be large enough to accomodate the driven section 66 of the stirring rod 60 so that the rod 60 can freely rotate, however, the aperture 44 should not be so large that the rod 60 wobbles. Details of the synchronous motor assembly 70 are clearly illustrated in exploded perspective view in FIG. 5 and in detailed views in FIGS. 6A, 6B and 6C.

Stirring rod 60 includes a top end 68, a rotor driven section 66, a fulcrum section 64 and a liquid immersed free end 62.

The middle or fulcrum section 64 is held in position by a flexible sealing diaphragm 46.

A brass weight 106 sits over top end 68 and is held in position by a rubber washer 104 such as illustrated in FIG. 5. Weight 106 has a thimble-like shape and weighs about 30 grams according to the preferred embodiment of the invention. By properly selecting the size and position of weight 106 it is possible to tune the natural frequency of rod 60 to equal the 300 r.p.m. speed of the motor. The rod 60 suspended by a diaphragm 46 acts as a classical conical pendulum. Maximum energy transfer occurs when the impedance of the rod 60 matches the impedance of the drive system 70.

Diaphragm 46 preferably comprises a silicone rubber material of the sort known to those of ordinary skill in the art and includes a rod engaging aperture 45 and an internal circular groove 47 near the periphery thereof. Circular groove 47 engages the circumferential flange 49 which extends perpendicularly outward from one end of cylindrical element 48. The other end 51 of cylindrical element 48 includes a plurality of machine threads 53 which receive a large screw down nut 52. Sealing washer 50 is located above flange 49 and below the underside of cap 20. Cap 20 includes a hole 21 which extends through cap mounting plate 22. Hole 21 is smaller in diameter than the outside diameter of either screw down nut 52 or diaphragm 54. Therefore it is possible to securely attach diaphragm 46 to cap 20 by mounting the circular groove 47 of a diaphragm 46 on flange 49 in the manner shown in FIGS. 7A and 7B and then passing cylindrical element 48 through washer 50 and cap hole 21 and then securing it in place by screwing down on nut 52.

In operation the plug 36 is connected to a conventional power source 74. Alternatively, if angular velocity control is important, the plug 36 can be connected to a conventional variable frequency source 72. Power is delivered to a stator element 38 by cord 34. Capacitor 32 produces a current that is approximately 90° out-of-phase with the incoming line current. This is a standard technique used with many conventional synchronous motors. See FIG. 10 for the electrical schematic details. The electrical power supplied to the winding of stator 38 sets up a synchronous rotating field which revolves at a speed of 300 revolutions per minute. Rotor 40 is forced to rotate at a speed that is in synchronism, i.e. identical with, the field established by the stator 38. The rotor 40 floats within gap 56 in such a fashion as to generate the minimal amount of heat and friction. Gap 51 may include a Teflon ® bearing or may be grease filled. As rotor 40 revolves it carries eccentrically located aperture 44 in a circular path around its axis of rotation 41. Therefore section 66 of the stirring rod 60 is driven in an orbiting circular path.

Figure 8B:
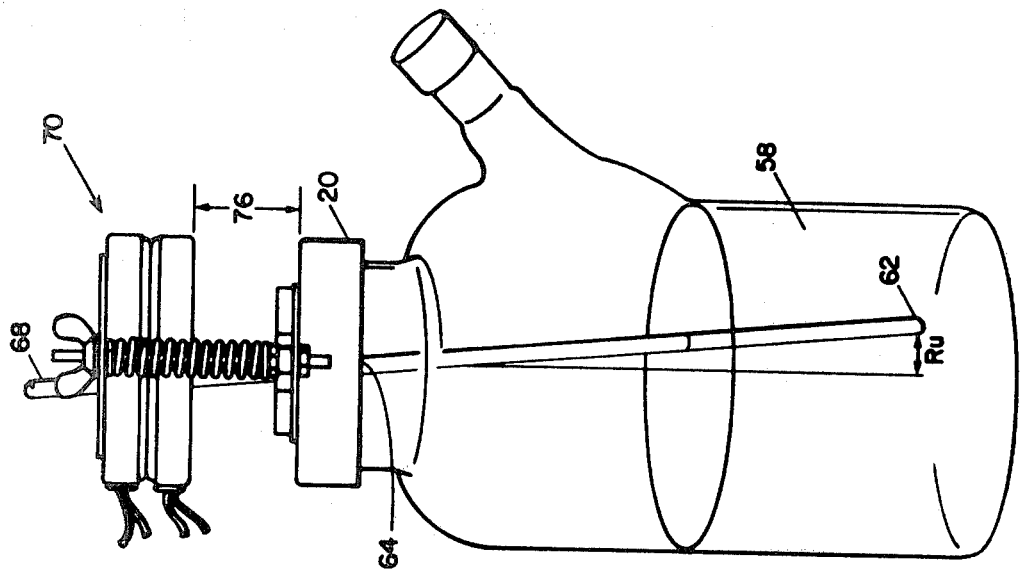
FIG. 8B is a partial cross sectional schematic view showing the device with the synchronous motor in its extreme upper position.

The fulcrum section 64 of stirring rod 60 is held firmly in position by diaphragm 46. Fulcrum section 64 has virtually no lateral freedom of movement though it does permit considerable angular rotation of the stirring rod 60. Therefore, if the stirring rod 60 is thought of as a lever, the circular motion imparted to section 66 is duplicated by the liquid immersed free end 62. The angular speed of the free tip 62 is identical to the angular speed of the top end 68, however, the linear speed of free tip 62 is proportional to the distance between the fulcrum section 64 and the driven section 66. Generally the smaller the distance between the fulcrum 64 and the driven portion 66, the higher the linear velocity of the free tip 62. The distance between the fulcrum 64 and the driven portion 66 is referred to by element number 76 and is directly proportional to the distance between cap 20 and the synchronous motor assembly 70. Note FIG. 8A. Conversely, as distance 76 is made larger, as shown in FIG. 8B, the linear velocity of the free tip 62 decreases.

This effect can be better understood by observing the effect of increasing or decreasing gap 76 upon the radius of rotation R of the free end 62.

Figure 8A:
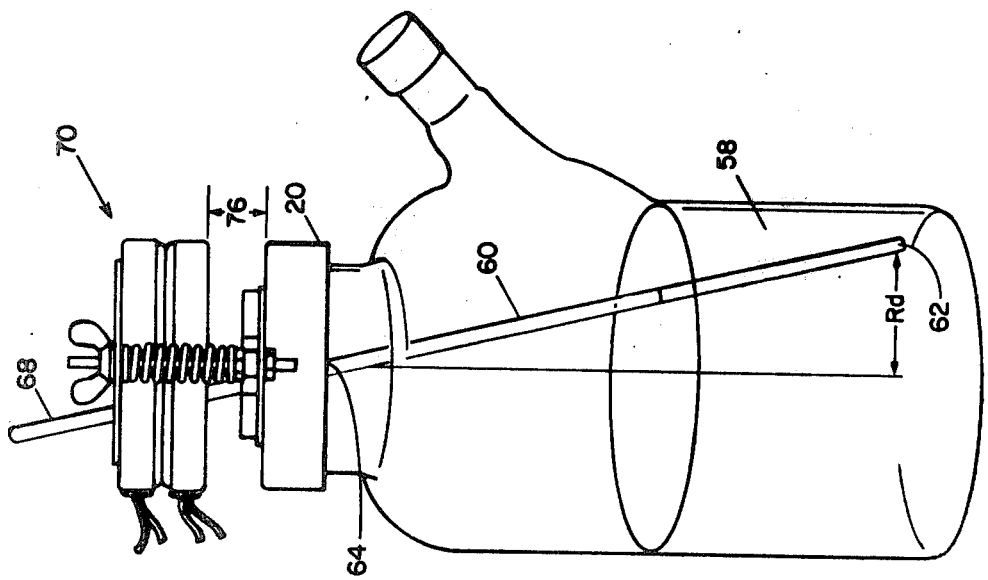
FIG. 8A is a partial cross sectional schematic view showing the device with the synchronous motor in its extreme downward position.

As the distance 76 is decreased as shown in FIG. 8A, the radius of the free tip 62 increases. The radius R of free tip 62 with the motor assembly 70 in the "down" position is referred to as $R_d$ in FIG. 8A. Alternatively, as the distance 76 is increased as shown in FIG. 8B, the radius R of the free tip 62 decreases. The radius R of the free tip 62 with the motor assembly 70 in the "up" position is referred to as $R_u$ in FIG. 8B. Therefore, $R_d$ is greater than $R_u$. The angular velocity of the free tip 62 is constant regardless of the vertical location of the motor assembly since the angular velocity is established by the synchronous speed of rotor 40. The linear velocity is established by the synchronous speed of rotor 40. The linear velocity of free end 62 is directly proportional to the product of the radius R and the angular velocity of rotor 40. Therefore, since the angular velocity is constant and $R_d$ is greater than $R_u$, it is clear that the linear speed of tip 62 increases as the motor assembly 70 is lowered, i.e. brought closer towards the cap 20. This is very important because it is the linear velocity of tip 62 that is significant, not the angular velocity, when it comes to damaging cells in a cell suspension culture. In a magnetic stirrer the velocity of the tip of the stirring bar is varied by varying the speed of the drive motor under the laboratory flask. In the present invention the linear speed of the free tip 62 may be varied by changing the distance 76 between the motor assembly 70 and the cap 20 by the appropriate adjustment of wing nuts 28. The speed of tip 62 can also be varied if the device is plugged into a variable frequency generator 72 such as illustrated in FIG. 1.

Figure 9:
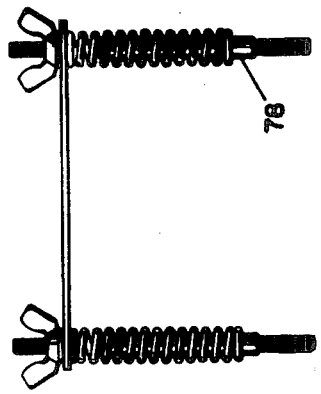
FIG. 9 is a detailed view of an alternative embodiment of the present invention in which a pair of tubular elements are used to stabilize the lateral motion of the device.

An alternative embodiment of the present invention is shown in FIG. 9. In that illustration of a pair of stabilizer tubes 78 are firmly attached to the lower side of motor mounting plate 30. Stabilizers 78 comprise a pair of tubular elements that extend downwardly and respectively surround stand off studs 24. Stabilizers 78 themselves are surrounded by springs 26. In this fashion the lateral wobble or tilt of the motor assembly 70 is limited by the stabilizers 78 which will impinge either on studs 24 or springs 26 if the wobble is too great.

Figure 11B:
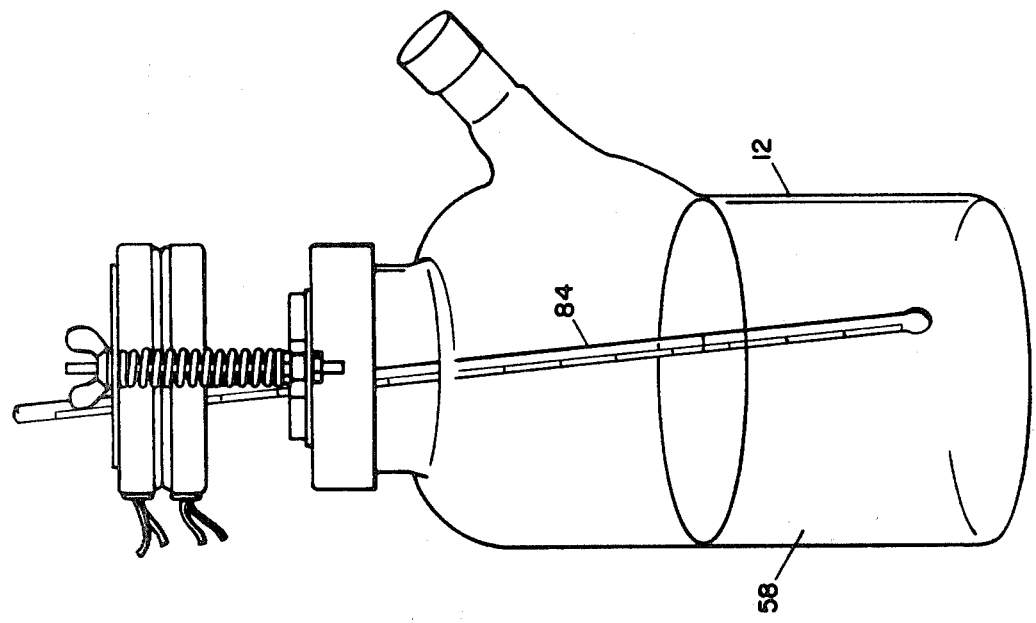
FIG. 11B is an alternative embodiment of the stirring rod in which a mercury-in-glass thermometer is employed as a stirring rod.
Figure 11A:
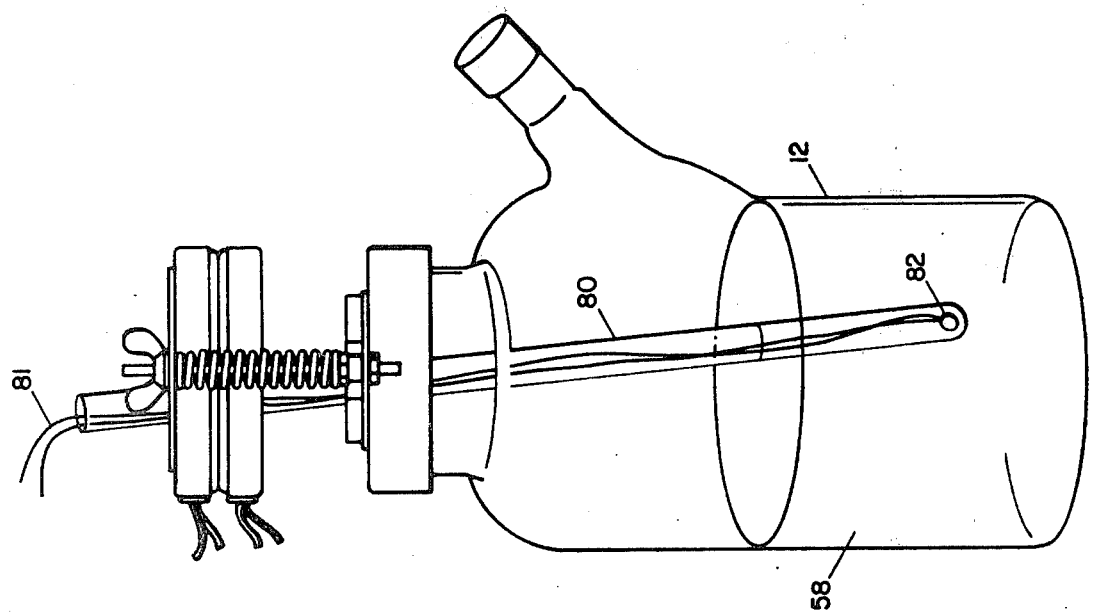
FIG. 11A is an elevated cross-sectional view of an alternative embodiment of the stirring rod in which a thermistor is included in the tip of the stirring element.
Figure 11D:
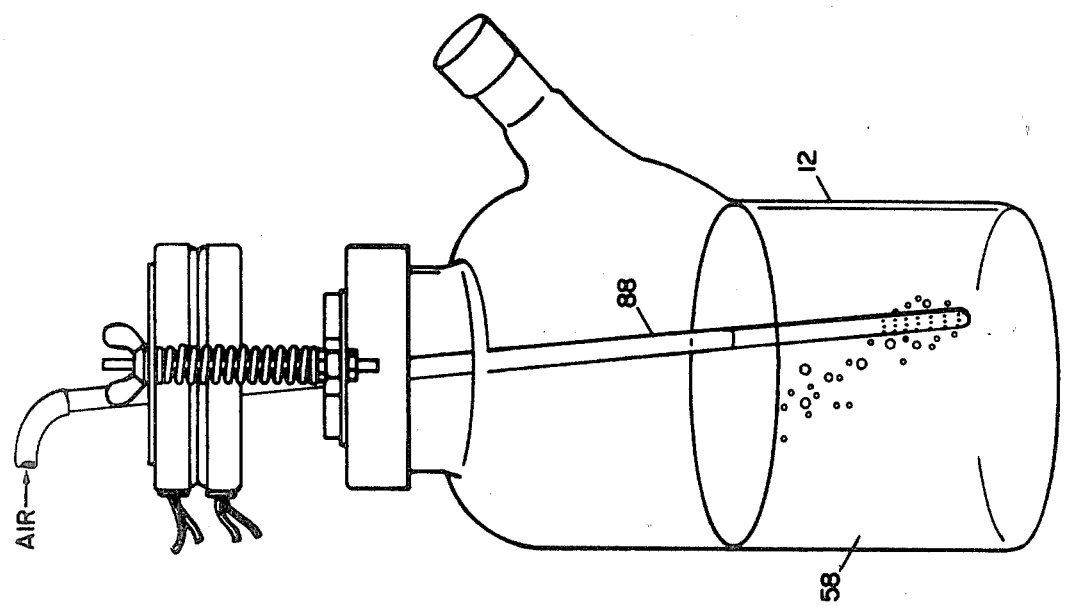
FIG. 11D is an alternative embodiment of the stirring rod in which the rod comprises a sparger.
Figure 11C:
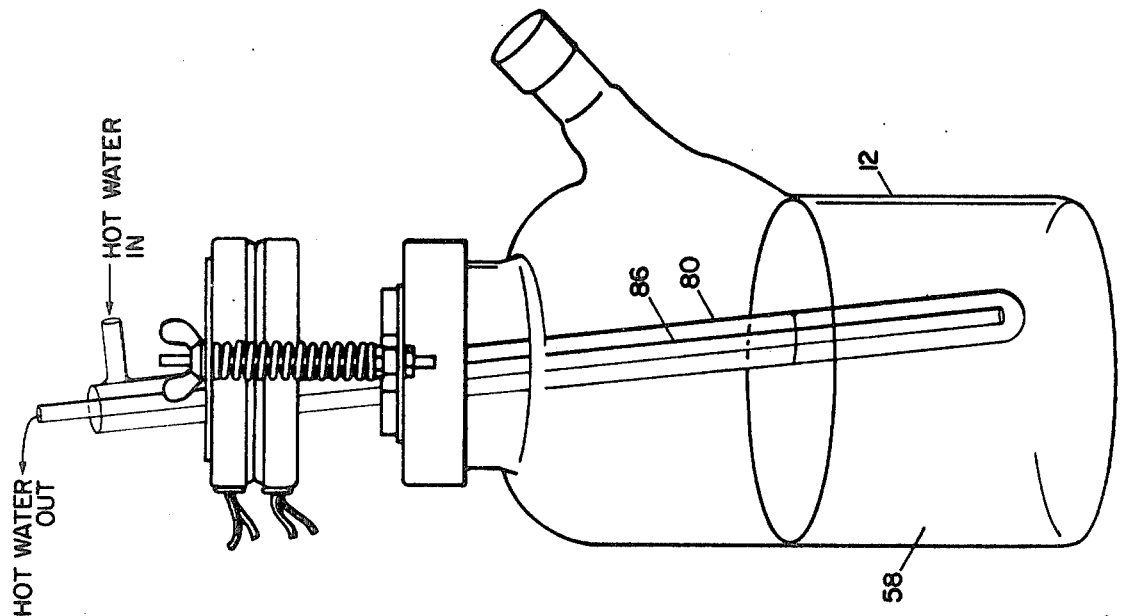
FIG. 11C is another alternative embodiment of the stirring rod in which the stirring rod comprises a heat exchanging device.

The device described, is not, of course, limited to the use of a stirring rod. Because of the relatively unique orbital motion of the rod it is possible to attach tubing or wires to the top of the stirring element. For example, tubing or wires could be connected to the top of a tube, the other end of which is immersed in the laboratory liquid 58. The sealed end could then include a thermistor element 82 which would continuously monitor the temperature of the laboratory liquid. See FIG. 11A. One could also use a mercury-in-glass thermometer 84 in place of the stirring rod. See FIG. 11B. In this manner no harm would come to the motor if the thermometers motion is manually arrested in order to read the temperature of the liquid 58. If a thermistor is used in the manner illustrated in FIG. 11A it would be possible to continuously control the heating current to maintain the temperature of the liquid 58 in the glass constant. It is also possible to use the stirring element 60 as a tubular heat exchanger as illustrated in FIG. 11C. According to that embodiment, the stirring element would consist of two concentric tubes with hot water running down between outer tube 80 and inner tube 86 and returning up inside the inner tube 86. According to yet another embodiment of the stirring rod element it would be possible to use the tube 80 as a sparger to bubble gases through the liquid 58 in the manner illustrated in FIG. 11D.

There are many advantages to the present invention. In particular, the device described herein generates very little heat because synchronous motors can be as much as 70% energy efficient and because the rotor of the device virtually floats in the magnetic field of the stator.

There are no bearing surfaces accessible to the cell culture medium. The heat generated with this type of drive can be as low as 1 to 2 watts which is a considerable improvement over other prior art devices. Furthermore, the direct action of the rotor on the stirring rod is a very simple and efficient form of linkage. It should be emphasized that the motor of the present invention is unique in that it has been deprived of its shaft and bearings in order to allow the stirring rod to pass through. This feature is important because it allows the user to adjust the vertical position of the glass rod with respect to the size of the vessel and it also makes it possible to adjust the linear velocity of the stirrer by changing the vertical location of the motor. The use of a synchronous motor is important because the angular velocity is always constant (300 r.p.m. in the case of the preferred embodiment).

While the invention has been described with reference to the preferred embodiment thereof it will be appreciated by those of ordinary skill in the art that changes may be made to the structure and function of elements without departing from the spirit and scope of the invention.

I claim:

1. A synchronous stirring apparatus for stirring liquid in a container with a stirring element, said apparatus comprising:
   cap means for attaching said apparatus to said container;
   a flexible sealing means attached to said cap means and to said stirring element for dependingly supporting said stirring element;
   a synchronous motor means attached to said cap means, said synchronous motor means including a stator means for producing a rotating field and a rotor means for rotating in synchronism with said rotating field about a defined axis of rotation;
   an eccentric means attached to said rotor means for engaging a section of said stirring element and driving said section in a circular path; and,
   stand-off means for attaching said synchronous motor means to said cap means, said stand-off means including an adjustment means for varying the distance between said synchronous motor means and said cap means.

2. The apparatus of claim 1 wherein said stand-off means comprises:
   a mounting plate attached to said cap means;
   a mounting plate attached to said synchronous motor means;
   at least two threaded stud means attached to said plate attached to said cap means and receivable in holes in said plate attached to said synchronous motor means;
   at least two spring means respectively surrounding said stud means and located between said plate attached to said cap means and said plate attached to said synchronous motor means; and,
   wherein said adjustment means comprise at least two threaded nut means respectively threadably attached to said two stud means on the side of said plate attached to said synchronous motor means opposite from said two spring means.

3. The apparatus of claim 2 further including:
   at least two tubular stabilizing means attached to said plate connected to said synchronous motor means and located between said two stud means and said two spring means respectively.

4. A synchronous stirring apparatus for stirring liquid in a container with a stirring element, said apparatus comprising:
   cap means for attaching said apparatus to said container;
   a flexible sealing means attached to said cap means and to said stirring element for dependingly supporting said stirring element;
   a synchronous motor means attached to said cap means, said synchronous motor means including a stator means for producing a rotating field and a rotor means for rotating in synchronism with said rotating field about a defined axis of rotation; and,
   an eccentric means attached to said rotor means for engaging a section of said stirring element and driving said section in a circular path, said eccentric means lying in a plane substantially perpendicular to said axis of rotation of said rotor and including an aperture means therein for receiving said stirring element,
   wherein the major axis of said stirring element and the axis of rotation of said rotor pass through said eccentric means at different locations.

5. The apparatus of claim 4 wherein said rotor is a permanent magnet.

6. A synchronous stirring apparatus for stirring liquid in a container with a stirring element, said apparatus comprising:
   cap means for attaching said apparatus to said container;
   a flexible sealing means attached to said cap means and to said stirring element for dependently supporting said stirring element, said flexible sealing means comprising a diaphragm having a circular groove therein;
   a synchronous motor means attached to said cap means, said synchronous motor means including a stator means for producing a rotating field and a rotor means for rotating in synchronism with said rotating field about a defined axis of rotation;
   eccentric means attached to said rotor means engaging a section of said stirring element and driving said section in a circular path;
   a cylindrical means having threads at one end and a circumferential flange around the other end thereof for engaging said circular groove in said diaphragm;
   a sealing washer receivable over said cylindrical means;
   a mounting plate attached to said cap means; and,
   a nut means for attaching said threaded portion of said cylindrical means to said cap means and to said mounting plate.

7. The apparatus of claim 6 wherein said diaphragm comprises a silicone rubber material.

8. A synchronous stirring apparatus for stirring liquid in a container with a stirring element, said apparatus comprising:
   cap means for attaching said apparatus to said container;
   a flexible sealing means attached to said cap means and to said stirring element for dependingly supporting said stirring element;
   a synchronous motor means attached to said cap means, said synchronous motor means including a stator means for producing a rotating field and a rotor means for rotating in synchronism with said rotating field about a defined axis of rotation;
   an eccentric means attached to said rotor means for engaging a section of said stirring element and driving said section in a circular path;
   wherein said stirring element comprises a tubular means having an electrically sensitive temperature sensing element at one end thereof and connecting wires at the other end thereof.

9. A synchronous stirring apparatus for stirring liquid in a container with a stirring element, said apparatus comprising:
   cap means for attaching said apparatus to said container;
   a flexible sealing means attached to said cap means and to said stirring element for dependingly supporting said stirring element;
   a synchronous motor means attached to said cap means, said synchronous motor means including a stator means for producing a rotating field and a rotor means for rotating in synchronism with said rotating field about a defined axis of rotation;
   an eccentric means attached to said rotor means for engaging a section of said stirring element and driving said section in a circular path,
   wherein said stirring element comprises a mercury-in-glass thermometer.

10. A synchronous stirring apparatus for stirring liquid in a container with a stirring element, said apparatus comprising:
    cap means for attaching said apparatus to said container;
    a flexible sealing means attached to said cap means and to said stirring element for dependingly supporting said stirring element;
    a synchronous motor means attached to said cap means, said synchronous motor means including a stator means for producing a rotating field and a rotor means for rotating in synchronism with said rotating field about a defined axis of rotation;
    an eccentric means attached to said rotor means for engaging a section of said stirring element and driving said section in a circular path,
    wherein said stirring element comprises a tubular heat exchanger consisting of two concentric tubes and wherein a temperature controlled liquid runs between the inner and outer tubes and returns inside the inner tubes.

11. A synchronous stirring apparatus for stirring liquid in a container with a stirring element, said apparatus comprising:
    cap means for attaching said apparatus to said container;
    a flexible sealing means attached to said cap means and to said stirring element for dependingly supporting said stirring element;
    a synchronous motor means attached to said cap means, said synchronous motor means including a stator means for producing a rotating field and a rotor means for rotating in synchronism with said rotating field about a defined axis of rotation;
    an eccentric means attached to said rotor means for engaging a section of said stirring element and driving said section in a circular path,
    wherein said stirring element comprises a sparger for bubbling gas through said liquid.

12. A synchronous stirring apparatus for stirring liquid in a container with a stirring element, said apparatus comprising:
    cap means for attaching said apparatus to said container;
    a flexible sealing means attached to said cap means and to said stirring element for dependingly supporting said stirring element;
    a synchronous motor means attached to said cap means, said synchronous motor means including a stator means for producing a rotating field and a rotor means for rotating in synchronism with said rotating field about a defined axis of rotation;
    an eccentric means attached to said rotor means for engaging a section of said stirring element and driving said section in a circular path; and,
    a Teflon ® bearing located between said rotor means and said stator means.

13. A synchronous stirring apparatus for stirring a fluid with an elongated stirring member having one end thereof immersed in said fluid, said apparatus comprising:
    means for pivotally supporting said stirring member at a position spaced away from said end;
    a hollow rotor having an axis of rotation;
    a disc attached to said rotor, said disc having an aperture therethrough which loosely receives said stirring member, said aperture being located eccentrically with respect to the axis of rotation of said rotor; and,
    means for driving said rotor, said means for driving said rotor comprising the stator of a two-phase electric synchronous motor.

14. The apparatus of claim 13 wherein said rotor comprises a cylinder having permanent magnetic poles around its outer surface which can be kept in rotation by an applied revolving magnetic field generated by said stator.

15. A synchronous stirring apparatus for stirring a fluid with an elongated stirring member having one end thereof immersed in said fluid, said apparatus comprising:
    means for pivotally supporting said stirring member at a position spaced away from said end;
    a hollow rotor having an axis of rotation;
    a stirring member drive means attached to said rotor, said stirring member drive means having an aperture therethrough which loosely receives said stirring member, said aperture being located eccentrically with respect to the axis of rotation of said rotor; and
    means for driving said rotor, said means for driving said rotor comprising the stator of an electric synchronous motor,
    wherein said stirring member passes through the hollow portion of said rotor.

* * * * *